(12) United States Patent
Heinz

(10) Patent No.: US 7,850,732 B2
(45) Date of Patent: Dec. 14, 2010

(54) SACRAL PROSTHESIS AND SURGICAL METHOD

(75) Inventor: Eric S. Heinz, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 570 days.

(21) Appl. No.: 11/608,852

(22) Filed: Dec. 11, 2006

(65) Prior Publication Data

US 2008/0140200 A1 Jun. 12, 2008

(51) Int. Cl.
*A61F 2/44* (2006.01)

(52) U.S. Cl. .............................. 623/17.11; 623/17.16

(58) Field of Classification Search ......... 606/279–299, 606/70–71; 623/17.11–17.16
See application file for complete search history.

(56) References Cited

U.S. PATENT DOCUMENTS

| | | | |
|---|---|---|---|
| 4,773,402 A * | 9/1988 | Asher et al. ................ | 606/250 |
| 4,800,874 A | 1/1989 | David et al. | |
| 5,108,397 A | 4/1992 | White | |
| 5,127,912 A * | 7/1992 | Ray et al. ................... | 606/250 |
| 5,300,073 A * | 4/1994 | Ray et al. ................... | 606/250 |
| 5,593,407 A * | 1/1997 | Reis .......................... | 606/261 |
| 5,626,616 A * | 5/1997 | Speece ....................... | 606/240 |
| 5,643,264 A | 7/1997 | Sherman et al. | |
| 5,810,815 A * | 9/1998 | Morales ...................... | 606/250 |
| 6,132,464 A * | 10/2000 | Martin ....................... | 623/17.15 |
| 6,197,028 B1 * | 3/2001 | Ray et al. ................... | 606/301 |
| 6,558,390 B2 | 5/2003 | Cragg | |
| 6,565,605 B2 * | 5/2003 | Goble et al. ............. | 623/17.11 |
| 6,635,059 B2 | 10/2003 | Randall et al. | |
| 7,282,064 B2 * | 10/2007 | Chin ......................... | 623/17.15 |
| 2003/0181982 A1 * | 9/2003 | Kuslich ..................... | 623/17.16 |
| 2003/0195518 A1 | 10/2003 | Cragg | |
| 2004/0158245 A1 * | 8/2004 | Chin ........................... | 606/61 |
| 2005/0267579 A1 * | 12/2005 | Reiley et al. ............. | 623/17.11 |

(Continued)

FOREIGN PATENT DOCUMENTS

EP 1415624 A1 5/2004

(Continued)

OTHER PUBLICATIONS

Zileli, Mehmet et. al., "Surgical Treatment of Primary Sacral Tumors: Complications Associated with Sacrectomy." Neurosurgical Focus, Nov. 2003, pp. 1-8, vol. 15, Article 9.

(Continued)

*Primary Examiner*—Thomas C Barrett
*Assistant Examiner*—Matthew Lawson

(57) ABSTRACT

A sacral prosthesis for a partial or complete sacrectomy has a central body with a platform on a superior face thereof; first and second arms extending superiorly and laterally from the central body, with the arms including respective terminal portions for anchoring to a respective ilium. The terminal portions are held spaced from one another and the central body is suspended by the arms such that the platform is disposed inferiorly to the terminal portions at a fixed position relative thereto. The sacral prosthesis supports a spinal column against inferior displacement by supporting a vertebral body with the platform, while advantageously simultaneously preventing relative lateral displacement of the ilia. The sacral prosthesis may advantageously be formed of a radiolucent material.

29 Claims, 7 Drawing Sheets

U.S. PATENT DOCUMENTS

| | | | |
|---|---|---|---|
| 2006/0224159 A1* | 10/2006 | Anderson | 606/61 |
| 2006/0241591 A1 | 10/2006 | Biscup et al. | |
| 2006/0265070 A1* | 11/2006 | Stinson et al. | 623/17.11 |
| 2007/0161993 A1* | 7/2007 | Lowery et al. | 606/61 |
| 2007/0191834 A1* | 8/2007 | Bruneau et al. | 606/61 |
| 2007/0203491 A1* | 8/2007 | Pasquet et al. | 606/61 |
| 2007/0233256 A1* | 10/2007 | Ohrt et al. | 623/17.11 |
| 2009/0018662 A1* | 1/2009 | Pasquet et al. | 623/17.16 |
| 2009/0216276 A1* | 8/2009 | Pasquet | 606/249 |

FOREIGN PATENT DOCUMENTS

| | | |
|---|---|---|
| WO | 2004/039283 A2 | 5/2004 |

OTHER PUBLICATIONS

"International Search Report," International Application No. PCT/US2007/086736, Apr. 7, 2008, European Patent Office, Rijswiijk, Netherlands.

\* cited by examiner

SACRAL PROSTHESIS AND SURGICAL METHOD

BACKGROUND

The invention relates to a sacral prosthesis and a method for a sacral prosthesis.

Removal of the sacrum, while undesirable, is sometimes necessary. For example, a malignant or benign tumor may be found in the sacrum, and removal of the sacrum may be the best treatment option. However, the sacrum performs two structural functions: vertically supporting the spine and securing the ilia of the pelvis against relative lateral displacement. Thus, during a sacrectomy surgical procedure, a surgeon may find it desirable to install an artificial construct for performing these structural functions. Typically, such a construct is custom made and involves the use of rods anchored to the ilia via the Galveston technique and joined to other rods anchored to the vertebrae of the spine. Installing such a custom made construct increases the complexity and time required for the surgical procedure.

While the above approach may be appropriate for some situations, there remains a need for alternative surgical methods and devices for replacing the sacrum, advantageously ones that artificially replace one or both of the functions of the sacrum.

SUMMARY

In one illustrative embodiment, a sacral prosthesis comprises a central body comprising a platform on a superior face thereof to support an inferior face of a lumbar vertebral body; first and second arms spaced from one another and extending superiorly and laterally from the central body in respective diverging directions; the first and second arms including respective terminal portions for anchoring to a respective ilium; the terminal portions held spaced from one another a first distance by the first and second arms in combination with the central body; and the central body is suspended by the arms such that the platform is disposed inferiorly to the terminal portions at a fixed position relative thereto. The central body may be generally wedge-shaped and generally taper, both anteriorly-posteriorly and laterally, toward an inferior portion thereof. The terminal portions may be disposed superiorly to the platform and may comprise at least one aperture to accept a bone screw extending therethrough to mount the sacral prosthesis to the ilia. At least one fastener may engage the central body to secure the central body to the lumbar vertebral body. The sacral prosthesis may advantageously be formed of a radiolucent material. Various other aspects and embodiments are disclosed, which may be used alone or in any combination.

In another embodiment, a surgical method comprises surgically resecting at least a portion, and optionally all, of a sacrum at a surgical site; disposing a sacral prosthesis in the surgical site such that the central body is disposed inferiorly to a lumbar vertebral body and between the ilia; securing the terminal portions to respective ilium; and supporting a spinal column against inferior displacement by supporting the vertebral body with the platform, while the sacral prosthesis simultaneously prevents relative lateral displacement of the ilia.

DETAILED DESCRIPTION

Figure 1:
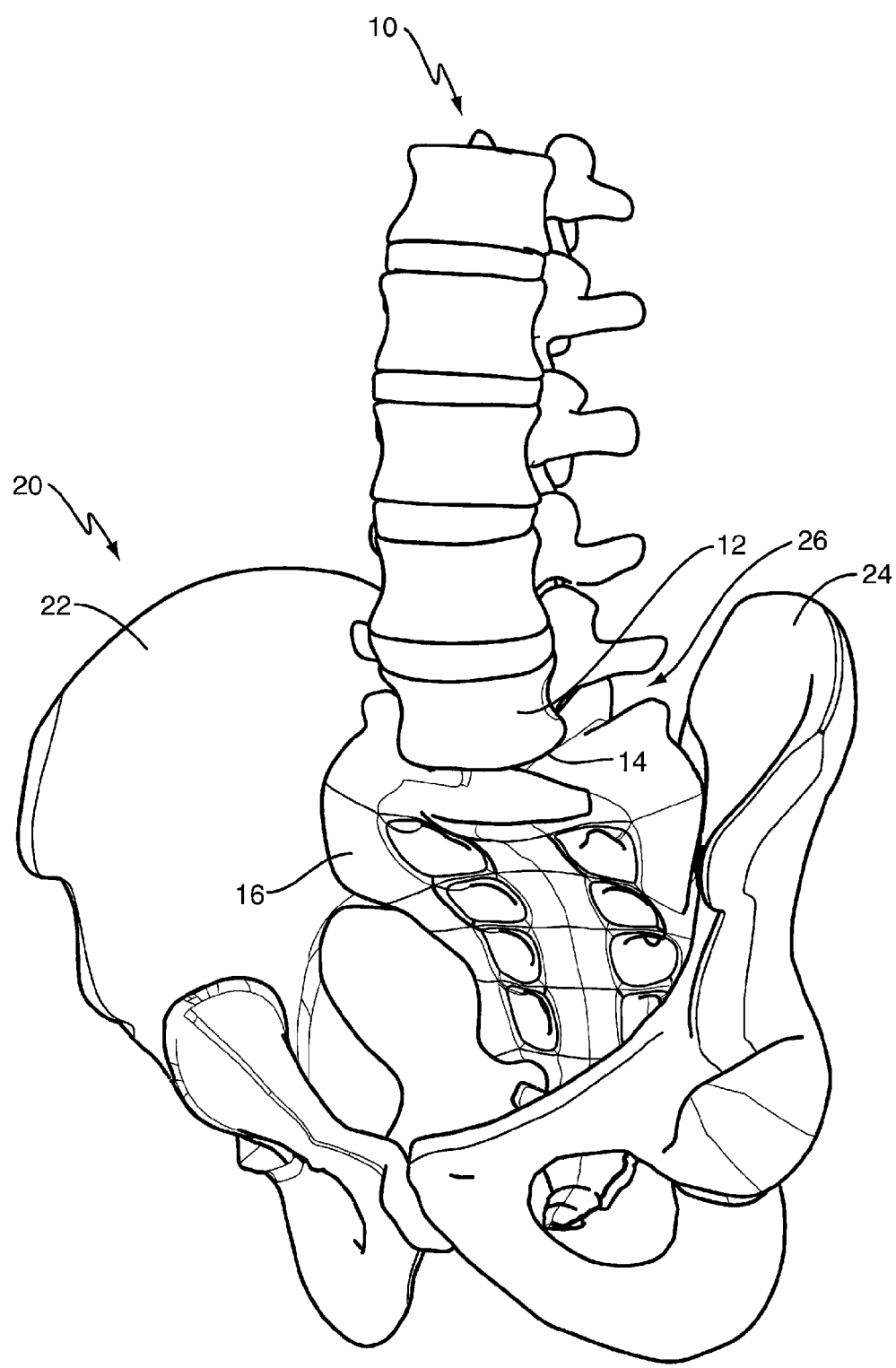
FIG. 1 shows a human pelvic girdle and partial spinal column.

The sacrum 16 is an inferior portion of the spinal column 10 that helps join the spinal column 10 to the pelvic girdle 20. The sacrum 16, in a healthy spine, provides a base that vertically supports the remainder of the spinal column 10 and typically directly supports the vertebra 12 in the lumbar region known as the L5 vertebra. In addition, the sacrum 16 helps maintain the pelvic girdle 20 against collapse. In particular, the sacrum 16 is disposed in the gap 26 between the right and left ilia 22, 24, and helps keep the posterior portions of the ilia 22,24 spaced from one another. As indicated above, it is sometimes necessary or desirable to remove the sacrum 16 for a variety of reasons. Illustrative embodiments of the present invention provide a sacral prosthesis 30 and/or a related surgical method.

One embodiment of the sacral prosthesis is shown in FIG. 1, and generally indicated at 30. The sacral prosthesis 30 comprises a central body 40 and a pair of arms 70a,70b extending from the body. The central body 40 is a somewhat elongated body that advantageously tapers from its superior portion 42 to its inferior tip portion 44, typically in both the anterior-posterior and lateral directions. Thus, the central body 40 is advantageously somewhat triangularly shaped, so as to mimic the sacrum 16 it replaces, but is typically somewhat shorter in length. The superior face 62 of the central body 40 forms a platform area 60. This platform area 60 is generally flat and may advantageously have a shape generally corresponding to the shape of the L5 vertebra 12. The face 62 of the platform area 60 may, if desired, include suitable texturing, such as small ridges, teeth, knurling, or the like, to aid in bonding the relevant vertebra 12 to the central body 40. In addition, one or more through holes 64 may extend through the central body 40 at the platform 60. These through holes 64 accept fasteners 54, as discussed further below, for securing the central body 40 to the spinal column 10. The central body's anterior face 48 may be generally flat, but may include a shallow, generally vertically oriented, depression 49 if desired. The posterior face 50 may be gently convexly curved and may include one or more recesses 52 that connect to the through holes 64. The lateral edges 46 of the central body 40, and indeed the entire exterior of the central body 40, are advantageously suitably contoured so as to remove sharp edges. The central body 40 may be solid or hollow, as is desired.

Figure 2:
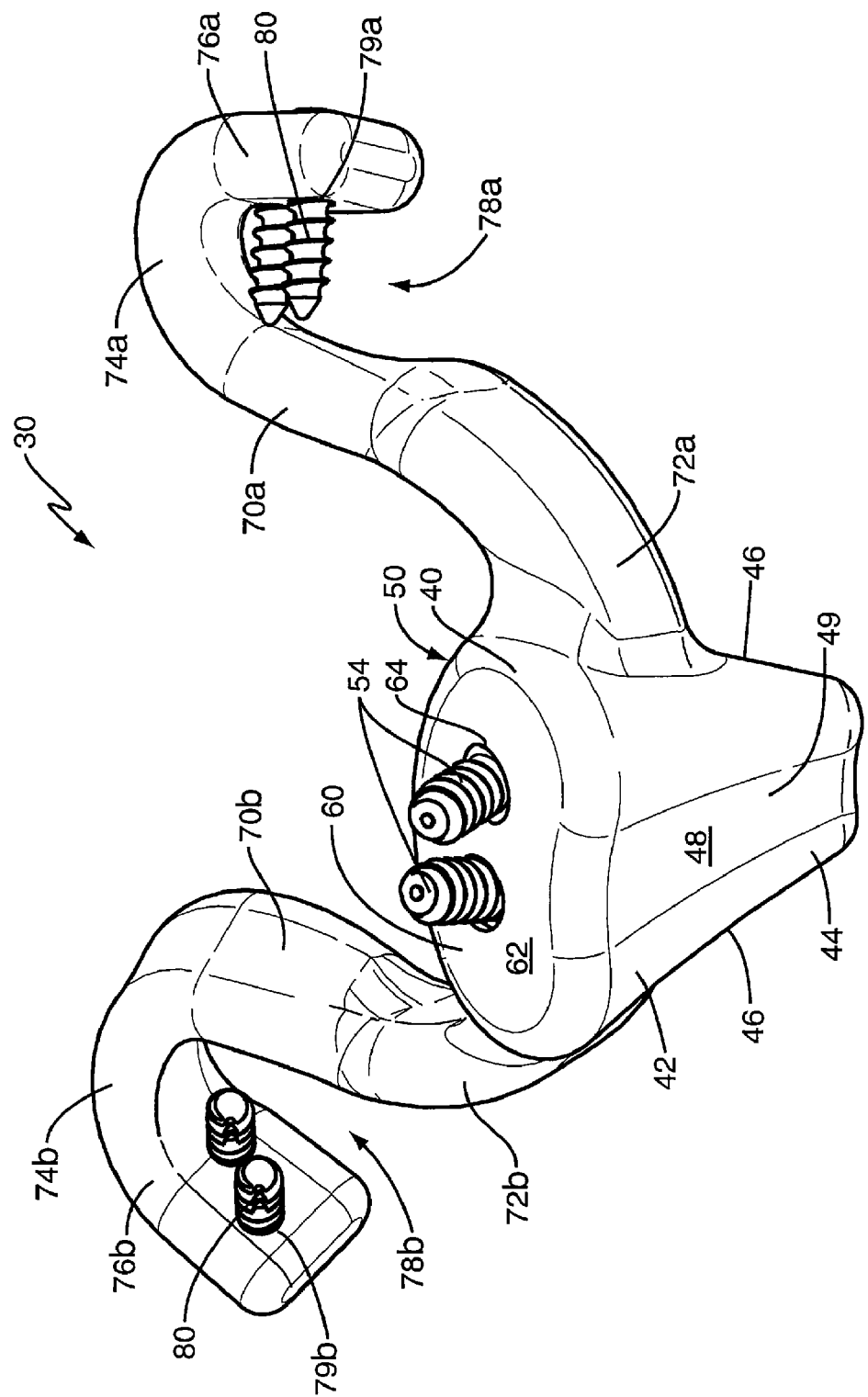
FIG. 2 shows a perspective view of a sacral prosthesis according to one embodiment of the present invention.
Figure 3:
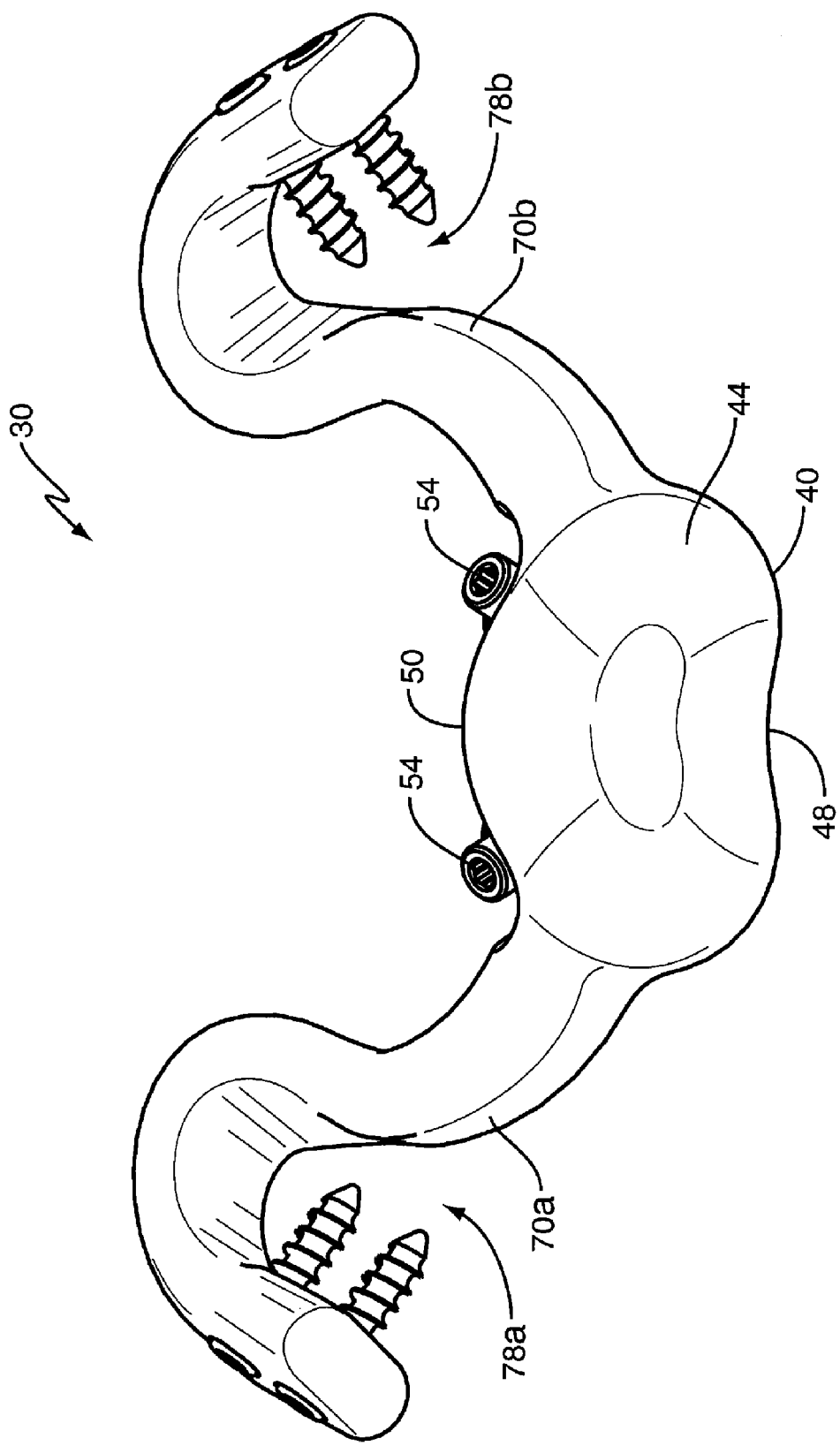
FIG. 3 shows a bottom view of the sacral prosthesis of FIG. 2.
Figure 4:
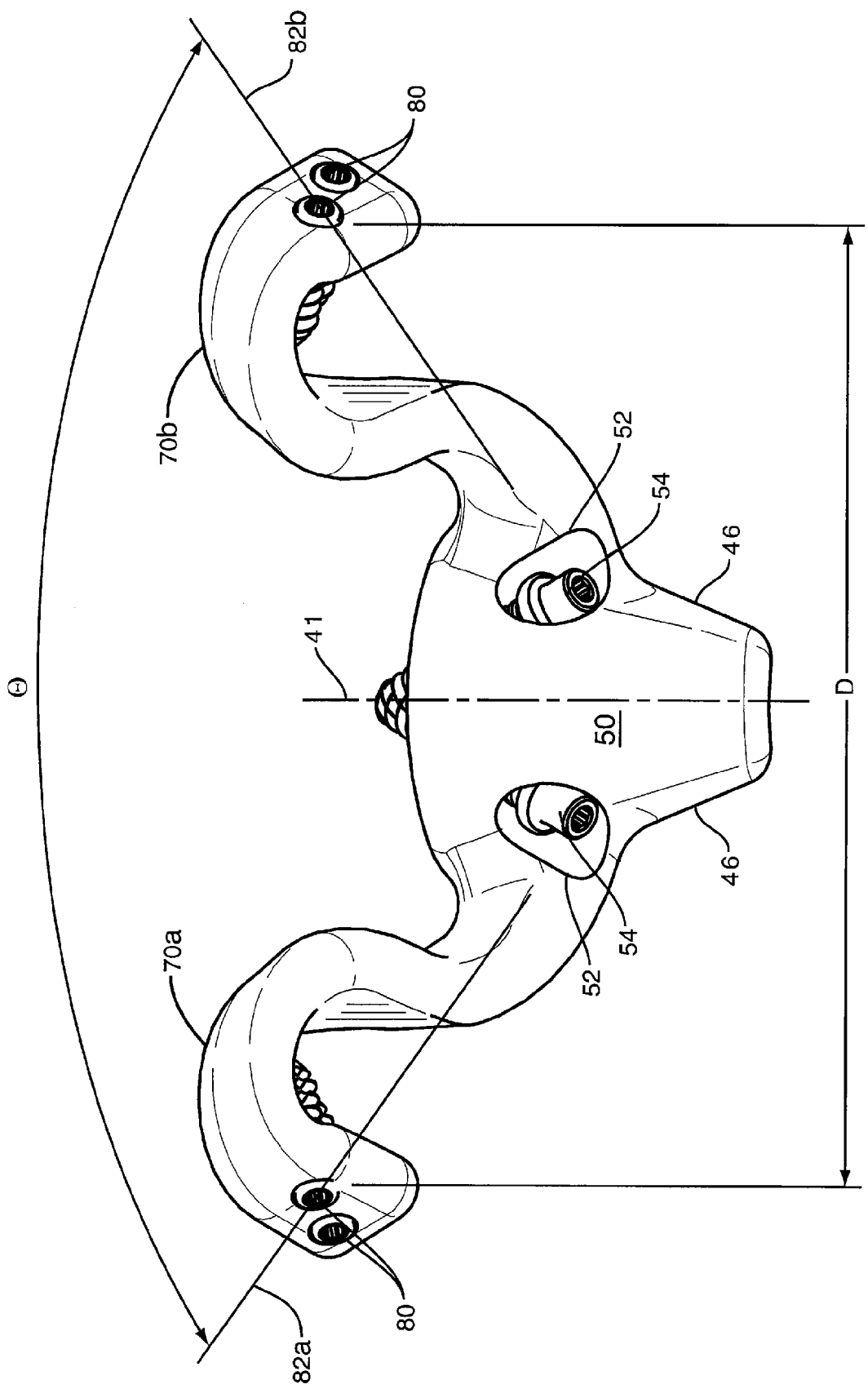
FIG. 4 shows a back view of the sacral prosthesis of FIG. 2.

The arms 70a,70b extend away from central body 40, proximate the platform area 60. For ease of reference, the arm that is intended to mate with the patient's right ilium 22 will be referred to in this description as the right arm 70b, and the arm intended to mate with the patient's left ilium 24 will be referred to in this description as the left arm 70a. Thus, in FIG. 2, the right arm 70b is on the left of the figure, while the left arm 70a is on the right of the figure. The left arm 70a includes a medial first section 72a disposed proximate the central body 40 and a lateral second section 74a disposed distal from the central body 40. The second section 72a includes a terminal portion 76a that is advantageously hooked-shaped with a hook gap 78a of sufficient width to fit over the corresponding ilium 24. The terminal portion 76a may advantageously include one or more holes 79a for corresponding anchor screws 80, as discussed further below. As can be seen in FIGS. 2-4, the left arm 70a is advantageously somewhat S-shaped overall, rather than straight. Nevertheless, a theoretical line 82a may be drawn from where the left arm 70a joins to the central body 40 to the point where the left arm 70a is to be anchored to the corresponding ilium 24. For the illustrated embodiment, this anchoring point may be the anchoring hole 79a closest to the central body 40.

The right arm 70b may be a substantial mirror image of the left arm 70a about central body midline 41. As such, the right arm 70b includes a medial first section 72b disposed proximate the central body 40 and a lateral second section 74b disposed distal from the central body 40. The second section 74b includes a terminal portion 76b that advantageously takes the form of a hooked section with a hook gap 78b of sufficient width to fit over the corresponding portion of the ilium 22. Terminal portion 76b may also include one or more holes 79b for corresponding anchor screws 80, as discussed further below. Again, a theoretical line 82b may be drawn from where the right arm 70b joins to the central body 40 to the point where the right arm 70b is to be anchored to the corresponding ilium 22. For the illustrated embodiment, this anchoring point may be the anchoring hole 79b closest to the central body 40.

Figure 5:
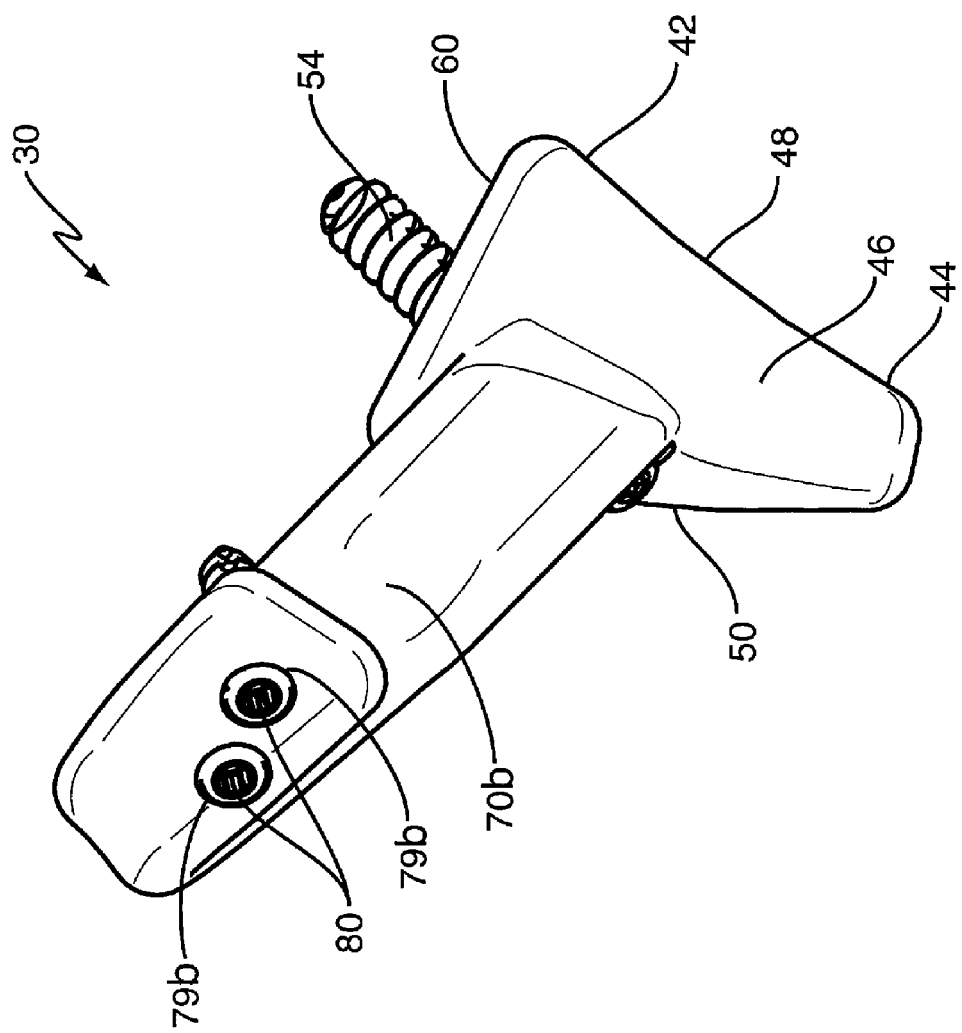
FIG. 5 shows a side view of the sacral prosthesis of FIG. 2.
Figure 7:
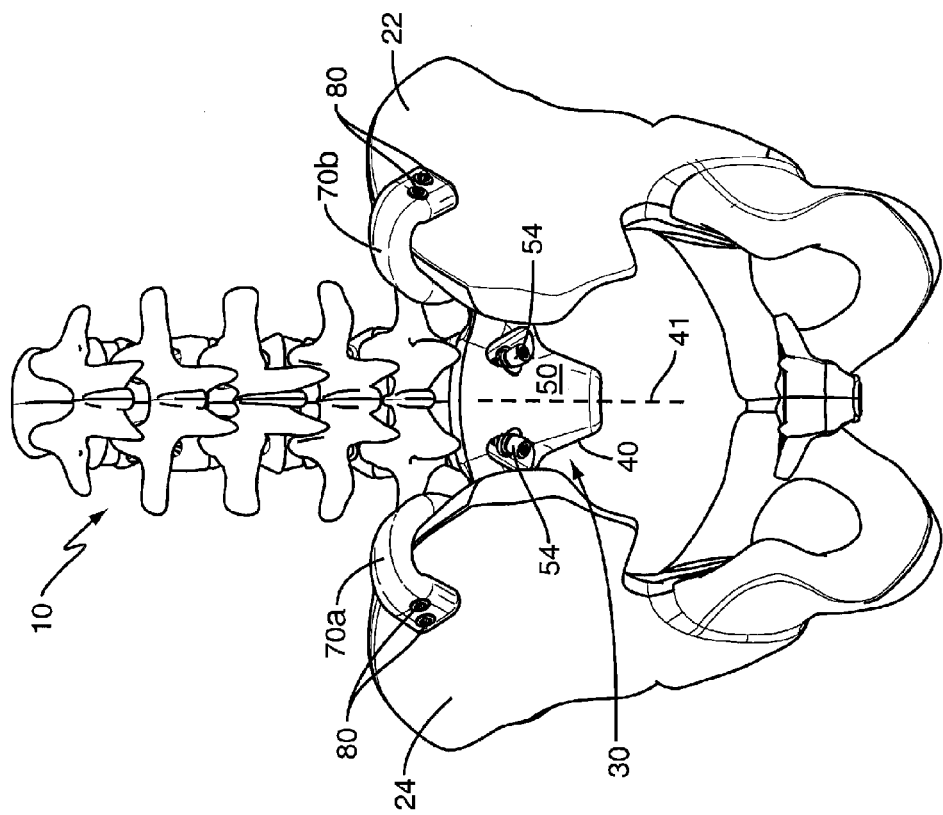
FIG. 7 shows a posterior view of the arrangement of FIG. 6.
Figure 6:
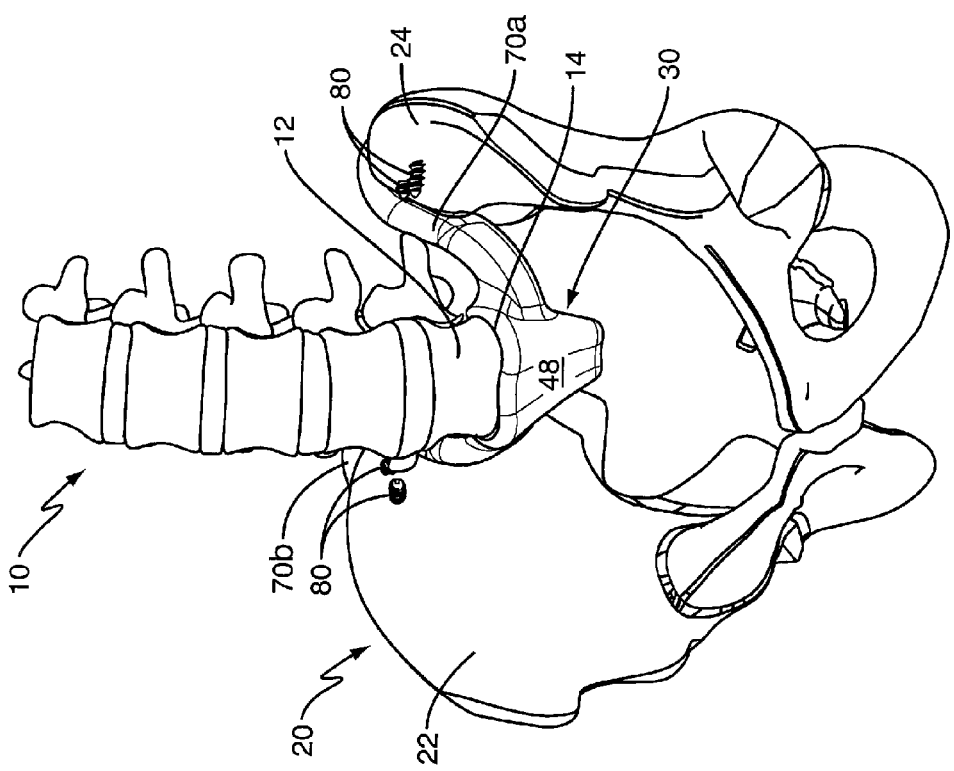
FIG. 6 shows an anterior perspective view the sacral prosthesis of FIG. 2 joined to a pelvic girdle and a spinal column.

The two arms 70a,70b extend away from the central body 40 at an angle so as to diverge therefrom. As can be seen in FIG. 4, the arms 70a,70b diverge such that lines 82a,82b are divergent and form an included angle Θ of approximately 75°-85°. In addition, as can be seen in FIG. 5, the lines 82a,82b may be disposed at a slight upward angle from the central body 40. This orientation is believed to facilitate installation and to route the arms 70a,70b away from sensitive neurovascular structures such as the sacral nerve roots. Further, as with the central body 40, the exterior surfaces of arms 70a,70b are advantageously suitably contoured so as to remove sharp edges.

The anchoring point 79a on one arm 70a is laterally spaced from the anchoring point 79b on the other arm 70b by distance D. The prosthesis 30 is advantageously designed to be rigid enough so that this distance D remains relatively fixed. Thus, it is contemplated that arms 70a,70b will be relatively substantial structures. To this end, it is contemplated that the sacral prosthesis 30 will be manufactured from a suitable biocompatible material, such as titanium, stainless steel, or carbon fiber reinforced polymer. It should be noted, however, that manufacturing the sacral prosthesis 30 from a radiolucent material may be advantageous because sacrectomy patients often require follow-up radiological studies such as CT scans and MRIs. As such, the sacral prosthesis 30 may be advantageously manufactured from a radiolucent material, such as carbon fiber reinforced polyetheretherketone known as PEEK Optima™, available from Invibio Limited of Lancashire, England. The sacral prosthesis 30 may be molded as a single piece, or may be made from separate pieces and welded or otherwise joined together, or may be formed using any other suitable known manufacturing technique.

The sacral prosthesis 30 is installed during a surgical procedure sometimes known as a sacrectomy. For this procedure, the surgeon prepares the surgical site and removes the sacrum 16 in a conventional fashion, typically using a combined anterior-posterior approach. See the article entitled "Surgical Treatment Of Primary Sacral Tumors: Complications Associated With Sacrectomy" by Dr. Mehmet Zileli et al., Neurosurgical Focus, volume 15, November 2003, which is incorporated herein by reference. The sacral prosthesis 30 is then positioned with the terminal portions 76a,76b hooking over the respective ilia 24,22 and the central body 40 disposed inferior to, and abutting, the L5 vertebra 12. Suitable screws 80 are then inserted through holes 79a,79b and into the respective ilia 24,22 to anchor the sacral prosthesis 30 to the pelvic girdle 20. Advantageously, the screws 80 pass through both exterior surfaces of the corresponding ilium, and are therefore installed using a bicortical technique. If desired, suitable holes in the ilia 22,24 may be drilled or otherwise created prior to installing the screws 80. Fasteners 54 are then inserted through their respective recesses 52 in the posterior face 50 of central body 40 so as to extend through the respective through hole 64. Again, if desired, suitable holes in the vertebra 12 may be drilled or otherwise created prior to installing the fasteners 54. These fasteners 54 are then tightened into the L5 vertebra 12 to secure the sacral prosthesis 30 to the spinal column 10. Of course, the sequence may be reversed, such that the sacral prosthesis 30 is first secured to the spinal column 10 and then secured to the ilia 22,24. Either way, the sacral prosthesis 30 is advantageously secured to both the spinal column 10 and the ilia 22,24. The surgeon then closes the surgical site in an appropriate manner.

The presence of the sacral prosthesis 30 provides vertical support to the spinal column 10. In particular, the spinal column 10 rests on the platform area 60 of the central body 40. The central body 40 is in turn supported by the arms 70a,70b which are anchored to the ilia 24,22. Thus, the spinal column 10 is vertically supported by the pelvic girdle 20 via the sacral prosthesis 30. In addition, the presence of the sacral prosthesis 30 helps prevent the pelvic girdle 20 from collapsing. The sacral prosthesis 30 provides resistance against the two anchoring points (e.g., at 79a,79b) moving toward or away from each other. Thus, the sacral prosthesis 30 performs the dual functions of supporting the spinal column 10 and maintaining the pelvic girdle 20. In addition, these two functions are provided by an easy-to-use device that requires neither extensive customization nor extensive assembly during surgery. As such, the surgical process is simplified. And, radiolucent versions of the sacral prosthesis 30 may aid in post-operative radiological studies by minimizing the scatter artifacts typically seen with metallic implanted materials. Further, some embodiments of the sacral prosthesis 30 allow the rectum to be protected more easily than in prior art sacrectomies.

Figure 8:
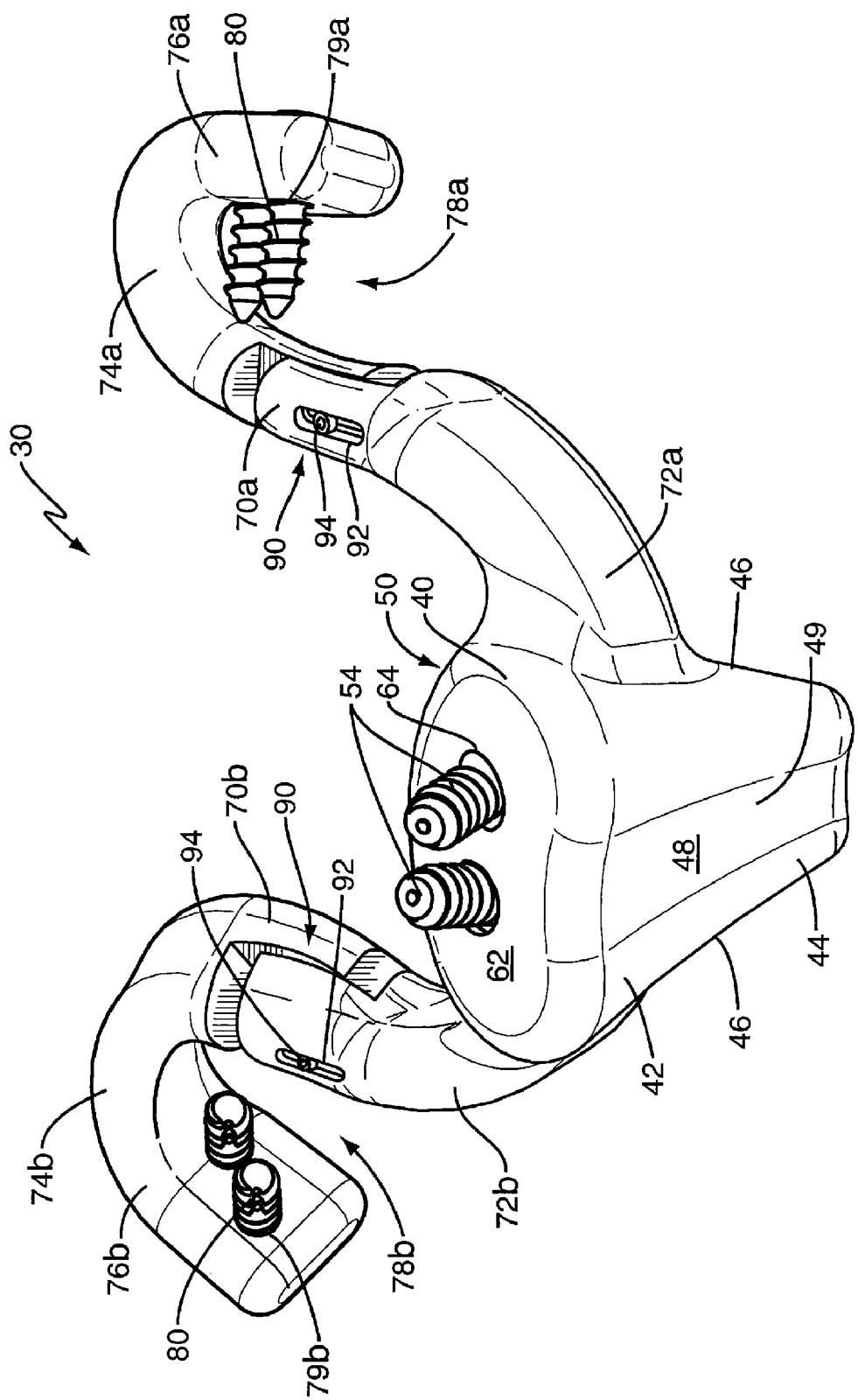
FIG. 8 shows a perspective view of a sacral prosthesis according to another embodiment of the present invention with lockably adjustable length arms.

The discussion above has assumed that the arms 70a,70b were of a fixed, non-varying length. However, in some embodiments, the arms 70a,70b may have a variable configuration. For example, as shown in FIG. 8, the each arm 70a,70b may include a lockable slide adjuster 90 that joins overlapping portions of the respective first sections 72a,72b and second sections 74a,74b. Looking at the right arm 70b, this slide adjuster 90 may include a slot 92 in the second section 74b with a screw 94 and slide nut (not shown) that is in a fixed position along the first section 72b. The left arm 70a likewise comprises a locking slide adjuster 90. With this arrangement, the length of the arms 70a,70b may be adjusted during surgery by sliding the second section 74a,74b relative to the first section 72a,72b and then locking the adjuster 90 by tightening the screw 94 to the slide nut. Of course, other lockable means for locking adjustment known in the art may alternatively be used, such as interlocking teeth and clamps, etc. The ability to vary the length of the arms 70a,70b allows the surgeon to easily adjust the sacral prosthesis 30 to the morphology of the patient. Thus, a single sacral prosthesis 30 design may be used for patients with differing gaps 26 between their ilia 22, 24.

The distal second sections 74a,74b of the arms 70a,70b may, if desired, include malleable sub-sections (not shown) that allow the hook shape of the terminal sections 76a,76b to be custom formed during surgery. For example, the surfaces of the arms 70a,70b in these malleable sub-sections may include a plurality of transverse grooves, or be made of a malleable material such as Nitinol, that allow the arms 70a, 70b to preferentially bend in these sub-sections. With such embodiments, the hook shapes in the terminal sections 76a, 76b may advantageously be formed to some nominal configuration at manufacture, and then adapted to a patient's particular needs during surgery using conventional in situ benders or other tools known in the orthopedic arts.

Further, the central body 40 may optionally include one or more passages therethrough, advantageously in the inferior portion 44 thereof, for the passage of a cable or other means for aiding in positioning the coccyx if the coccyx is to be left in place at the conclusion of the surgical procedure.

The discussion above has assumed that the sacral prosthesis 30 is secured to the spinal column 10 via fasteners 54, and that the L5 vertebra 12 directly abuts the platform area 60. However, it should be understood that additional means may be employed to secure the sacral prosthesis 30 to the spinal column 10, such as an application of appropriate bone cement between the platform area 60 and the inferior face 14 of the adjacent vertebra 12. Alternatively, the platform area 60 may be coated with an osteoconductive coating. Indeed, it is believed advantageous for the sacral prosthesis 30 to become fused to the adjacent vertebra 12 in most situations, not just fixedly mounted thereto.

The discussion above has also assumed that the sacrum 16 is being totally removed; however, this is not required in all embodiments. In some embodiments, the sacrum 16 may be only partially resected. In such situations, the amount resected should advantageously be sufficient to allow the central body 40 of the prosthesis 30 to be positioned in the space formerly occupied by the resected material.

The present invention may be carried out in other specific ways than those herein set forth without departing from the scope and essential characteristics of the invention. The present embodiments are, therefore, to be considered in all respects as illustrative and not restrictive, and all changes coming within the meaning and equivalency range of the appended claims are intended to be embraced therein.

What is claimed is:

1. A surgical method for a sacral prosthesis, comprising:
   providing a sacral prosthesis, said prosthesis comprising:
      a central body having a superior face forming a platform;
      first and second arms spaced from one another and extending superiorly and laterally from said central body;
      said first and second arms including respective terminal portions spaced from one another a first distance;
   surgically resecting at least a portion of a sacrum at a surgical site;
   disposing the sacral prosthesis in the surgical site such that said central body is disposed inferiorly to a lumbar vertebral body and between the ilia;
   securing said terminal portions to respective ilium;
   supporting a spinal column against inferior displacement by supporting said vertebral body with said platform, while said sacral prosthesis simultaneously prevents relative lateral displacement of said ilia; and
   inserting a fastener through an aperture in a posterior face of the central body, into a through opening in the central body, and through an aperture in the superior face of the central body.

2. The method of claim 1 wherein said securing said terminal portions to respective ilium comprises fastening said terminal portions to respective ilium via respective screws.

3. The method of claim 1 wherein said first arm is lockably adjustable in length, and further comprising adjusting a length of said first arm.

4. The method of claim 1 wherein said disposing the sacral prosthesis in the surgical site such that said central body is disposed inferiorly to a lumbar vertebral body comprises abutting said platform against an inferior face of said vertebral body.

5. The method of claim 1 wherein securing said central body to the vertebral body includes disposing the superior face of the central body against an inferior surface of said vertebral body and inserting a fastener through the aperture in the posterior face of the central body and into the vertebral body.

6. The method of claim 5 wherein said securing said central body to an inferior surface of said vertebral body comprises engaging the fastener with an inferior face of the vertebral body and tightening the fastener into said vertebral body.

7. The method of claim 1 wherein said terminal portions are hook-shaped, and further comprising hooking said terminal portions over respective ilia.

8. The method of claim 1 further comprising bending said arms to form said terminal sections into hook shapes.

9. The method of claim 1 wherein said sacral prosthesis is formed of a radiolucent material, and further comprising subsequently performing a post-operative radiological study of the surgical site.

10. The method of claim 1 wherein surgically resecting at least a portion of a sacrum comprises surgically resecting all of said sacrum.

11. A sacral prosthesis for implantation in a patient, comprising:
    a central body comprising a platform on a superior face thereof to support an inferior face of a lumbar vertebral body;
    the superior face faces in a superior direction towards a lumbar section of the patient when the prosthesis is implanted in the patient;
    first and second arms spaced from one another and extending superiorly and laterally from said central body in respective diverging directions;
    said first and second arms including respective terminal portions for anchoring to a respective ilium;
    said terminal portions held spaced from one another a first distance by said first and second arms in combination with said central body;
    the terminal portion of at least one of the first and second arms including a hook-shaped portion that forms a gap between generally opposing portions of the hook-shaped portion, the gap shaped to receive a portion of the respective ilium such that one of the opposing portions is disposed on a medial or anterior surface of the ilium and the other opposing portion is disposed on a lateral or posterior surface of the ilium when the prosthesis is attached to the patient;
    said central body suspended by said arms such that said platform is disposed inferiorly to said terminal portions at a fixed position relative thereto.

12. The sacral prosthesis of claim 11 wherein at least one of said first and second arms is lockably adjustable in length.

13. The sacral prosthesis of claim 11 wherein said central body and said arms are unitary.

14. The sacral prosthesis of claim 11 wherein said first and second arms are generally S-shaped.

15. The sacral prosthesis of claim 11 wherein said terminal portion of said first arm comprises an aperture and further comprising a bone screw extending through said aperture to secure said first arm to a respective ilium.

16. The sacral prosthesis of claim 11 further comprising a fastener extending through said central body to secure said central body to the lumbar vertebra.

17. The sacral prosthesis of claim 11 wherein said central body is made from a radiolucent material.

18. The sacral prosthesis of claim 11 wherein said platform is substantially flat.

19. The sacral prosthesis of claim 11:
wherein said first and second arms are generally S-shaped;
wherein said terminal portions of said arms are both hook shaped; and
wherein said central body and said arms are made from a radiolucent material.

20. A prosthesis for placement in a sacral space of a patient defined between two ilia and inferior to a lumbar vertebral body, the prosthesis comprising:
a central body configured to fit in the sacral space and comprising a platform on a superior face thereof;
the central body including a through opening having an aperture in a posterior face of the central body and an aperture in the superior face of the central body, the through opening being contained within the central body and having sidewalls that fully enclose the through opening, the posterior face of the central body faces directly away from the sacral space and opposes an anterior face that faces directly towards the sacral space when the prosthesis is placed in the patient;
first and second arms spaced from one another and extending superiorly and laterally from said central body in respective diverging directions;
said first and second arms comprising respective terminal portions for anchoring to respective ilia; said terminal portions spaced from one another a first distance;
wherein said first and second arms in combination with said central body are configured to maintain the ilia in spaced relation by constraining movement of the ilia relative to each other;
wherein said first and second arms in combination with said central body are further configured to support the spinal column by said platform supporting the lumbar vertebral body from below.

21. The prosthesis of claim 20 wherein said first and second arms are generally S-shaped.

22. The prosthesis of claim 20 wherein said central body is generally tapered, both anteriorly-posteriorly and laterally, toward an inferior portion thereof.

23. The prosthesis of claim 20 wherein said terminal portions comprise respective apertures and further comprising respective bone screws extending through said apertures to secure said arms to respective ilia.

24. The prosthesis of claim 20 further comprising a fastener disposed so as to extend through said central body to secure said central body to the lumbar vertebral body.

25. A sacral prosthesis for placement in a sacral space defined between two ilia and inferior to a lumbar vertebral body, the sacral prosthesis comprising:
a generally wedge-shaped central body forming a platform on a superior face thereof to support an inferior face of the vertebral body, the superior face faces in a superior direction towards the lumbar vertebral body when the sacral prosthesis is positioned in a patient; said central body generally tapering, both anteriorly-posteriorly and laterally, toward an inferior portion thereof, the inferior portion positioned farther from the lumbar vertebral body than the superior face when the sacral prosthesis is positioned in the patient;
first and second arms spaced from one another and extending superiorly and laterally from said central body; said first and second arms extending from said central body to respective ilia;
said first and second arms including respective hook-shaped terminal portions distal from said central body, configured to hook respective ilia;
each of said terminal portions comprising at least one aperture to accept a bone screw extending therethrough;
wherein said terminal portions are disposed superiorly to said platform;
at least one fastener engaging said central body to secure said central body to the lumbar vertebral body.

26. The prosthesis of claim 25 wherein at least one of said first and second arms is lockably adjustable in length.

27. The prosthesis of claim 25 wherein said central body and said arms are unitary.

28. The prosthesis of claim 25 wherein said central body and said arms are made from a radiolucent material.

29. The prosthesis of claim 25 wherein the central body includes at least one through opening for receiving the fastener, the opening having an aperture in a posterior face of the central body and an aperture in the superior face of the central body.

* * * * *